United States Patent
Henze et al.

(10) Patent No.: US 8,637,723 B2
(45) Date of Patent: *Jan. 28, 2014

(54) PROCESS FOR THE ACTIVATION OF A COPPER-, ZINC- AND ZIRCONIUM OXIDE-COMPRISING ADSORPTION COMPOSITION

(76) Inventors: Guido Henze, Tokyo (JP); Lothar Karrer, Pfungstadt (DE); David J. Artrip, Los Angeles, CA (US); Heiko Urtel, Bobenheim-Roxheim (DE); Stephan Hatscher, Syke (DE)

( * ) Notice: Subject to any disclaimer, the term of this patent is extended or adjusted under 35 U.S.C. 154(b) by 137 days.

This patent is subject to a terminal disclaimer.

(21) Appl. No.: 13/228,309

(22) Filed: Sep. 8, 2011

(65) Prior Publication Data

US 2012/0065452 A1    Mar. 15, 2012

Related U.S. Application Data

(60) Provisional application No. 61/381,081, filed on Sep. 9, 2010.

(51) Int. Cl.
 *C07C 7/12* (2006.01)
(52) U.S. Cl.
 USPC ............ 585/824; 585/823; 585/820; 585/826
(58) Field of Classification Search
 None
 See application file for complete search history.

(56) References Cited

U.S. PATENT DOCUMENTS

| | | | |
|---|---|---|---|
| 3,549,719 A | 12/1970 | Duyverman et al. | |
| 3,676,516 A | 7/1972 | Haskell et al. | |
| 4,713,090 A | 12/1987 | Yokoe et al. | |
| 4,917,711 A | 4/1990 | Xie et al. | |
| 7,511,080 B2 | 3/2009 | Green et al. | |
| 2005/0241478 A1 | 11/2005 | Junicke et al. | |
| 2012/0065451 A1 | 3/2012 | Henze et al. | |

FOREIGN PATENT DOCUMENTS

| | | |
|---|---|---|
| CN | 1191772 | 9/1998 |
| DE | 1 929 977 A1 | 12/1969 |
| DE | 0 153 761 A5 | 2/1982 |
| DE | 199 63 441 A1 | 7/2001 |
| EP | 296 734 A1 | 12/1988 |
| EP | 537 628 A2 | 4/1993 |
| WO | WO-95/21146 A1 | 8/1995 |
| WO | WO-02/068119 A1 | 9/2002 |
| WO | WO-2004/022223 A2 | 3/2004 |
| WO | WO-2007/093526 A2 | 8/2007 |
| WO | WO-2012/032475 A1 | 3/2012 |

OTHER PUBLICATIONS

International Search Report & Written Opinion—PCT/IB2011/053909—Sep. 7, 2011 mailed Jan. 19, 2012.

*Primary Examiner* — Tam M Nguyen
(74) *Attorney, Agent, or Firm* — Novak Druce Connolly Bove + Quigg LLP

(57) ABSTRACT

The invention relates to a process for the activation of a copper, zinc and zirconium oxide-comprising adsorption composition for the adsorptive removal of carbon monoxide from substance streams comprising carbon monoxide and at least one olefin wherein
(i) in a first activation step an activation gas mixture comprising the olefin and an inert gas is passed through the adsorption composition, and
(ii) in a second activation step the adsorption composition is heated to a temperature in the range from 180 to 300° C. and an inert gas is passed through it,
wherein the steps (i) and (ii) can each be performed several times.

4 Claims, 4 Drawing Sheets

PROCESS FOR THE ACTIVATION OF A COPPER-, ZINC- AND ZIRCONIUM OXIDE-COMPRISING ADSORPTION COMPOSITION

CROSS-REFERENCE TO RELATED APPLICATION

This application claims the benefit of U.S. Provisional Application Ser. No. 61/381,081 filed Sep. 9, 2010, the entire contents of which are incorporated herein by reference in its entirety.

FIELD OF THE INVENTION

The invention relates to a process for the activation of a copper, zinc and zirconium oxide-comprising adsorption composition for the adsorptive removal of carbon monoxide from carbon monoxide-comprising substance streams and a process for the removal of carbon monoxide from carbon monoxide-comprising substance streams comprising the activation of the adsorption composition.

BACKGROUND

In various sectors of industry, it is important to have especially pure substance streams available. Catalytic chemical reactions are one example. Catalysts are often very sensitive to poisoning. Thus, even exceptionally small quantities of impurities in the starting material stream can collect on the catalyst and poison it. Typically, for olefin polymerization reactions on modern catalysts, for example metallocene catalysts, olefin streams are required which comprise not more than a few ppb (parts per billion, i.e. $10^{-9}$ parts) of impurities per part of the desired substance ("polymer-grade" olefins). Olefins deriving from typical olefin sources (steam cracker, fluid catalytic cracker, dehydrations, MTO ("methanol to olefins") processes mostly have very much higher contents (ppm or even per-mille range) of impurities such as carbon monoxide or oxygen ("chemical grade"); these contents must be decreased appropriately before use for polymerization.

Typically, the substance streams to be purified are air, nitrogen or argon or hydro-carbons such as ethylene, propylene, 1-butene, 2-butene, 1,3-butadiene or styrene. Typical impurities which must as a rule be removed are oxygen and carbon monoxide, and often also water, carbon dioxide, hydrogen or even sulfur, arsenic or antimony compounds. Processes for the removal of such impurities from substance streams are known.

Many adsorptive processes and adsorbents for the removal of carbon monoxide from substance streams are known. The German laid-open specification DE 1 929 977 teaches catalysts comprising 20 to 60 parts of CuO to 100 parts of ZnO and the use thereof for the removal of CO from ethylene and propylene streams at a temperature in the range from 50 to 200° C. U.S. Pat. No. 3,676,516 teaches a supported Cu catalyst, whereof 20 to 95% of the copper is present as $Cu^{2+}$, and the use thereof for CO removal from ethylene or propylene streams at a temperature below about 200° C., and in the examples specifically at about 93° C. U.S. Pat. No. 4,917,711 discloses an adsorbent which comprises a copper compound on a high-surface-area support, but also adsorbs olefins and hence is only suitable for the purification of nitrogen, inert gases and saturated hydrocarbons.

WO 95/021146 A1 teaches a process for the removal of carbon monoxide and also arsine, if present, from liquid hydrocarbon streams by contacting with a sorbent which, depending on the embodiment, comprises dispersed copper at the oxidation levels 0, +1 or +2, and in certain cases also manganese dioxide. EP 537 628 A1 discloses a process for the removal of carbon monoxide from alpha olefins and saturated hydrocarbons by contacting with a catalyst system based on at least one oxide of a metal selected from Cu, Fe, Ni, Co, Pt and Pd and at least one oxide of a metal selected from groups 5, 6 or 7 of the periodic table of the elements at 0 to 150° C. U.S. Pat. No. 4,713,090 describes an adsorbent for obtaining high-purity carbon monoxide by pressure or temperature swing adsorption. The adsorbent comprises a composite support with a core of silicon or aluminum oxide and an outer layer of an activated charcoal on which a copper compound is supported.

WO 2004/022223 A2 teaches a copper-, zinc-, zirconium- and optionally aluminum-comprising adsorption composition and the use thereof for the removal of CO from substance streams in the completely reduced state.

Processes are also known for activating or reactivating catalysts, also those comprising copper, or passivating them for transport. DD 0 153 761 relates to a process for the activation or reactivation of iron molybdate redox catalysts, which can also comprise copper, wherein the catalysts are first calcined in a non-oxidizing atmosphere and then brought into contact with an oxidizing gas. DE 199 63 441 A1 teaches a process for the regeneration of copper-comprising hydrogenation catalysts by first oxidizing and then reducing treatment, wherein the reduction is preferably first performed in the hydrogenation reactor. WO 02/068 119 A1 discloses copper-comprising hydrogenation and dehydrogenation catalysts which are used in the reduced state and are passivated for transport by partial oxidation of the copper. EP 296 734 A1 describes copper-comprising shift or methanol catalysts which owing to reduction at a temperature below 250° C. have a Cu surface area of at least 70 m²/g based on copper.

WO 2007/093526 discloses a copper, zinc and zirconium oxide-comprising adsorption composition, where the copper-comprising fraction thereof has a reduction level, expressed as the weight ratio of metallic copper to the sum of metallic copper and copper oxides, calculated as CuO, of at least 45% and at most 75%, and a process for the removal of carbon monoxide from carbon monoxide-comprising substance streams by adsorption on this adsorption composition. An adsorption composition with a reduction level in the stated range is supposed to be especially regenerable.

WO 2007/093526 also discloses a process for the production of the adsorption composition by:
a) preparation of a solution of the components of the adsorption composition and/or of soluble starting compounds for these;
b) precipitation of a solid from this solution by addition of a base;
c) separation and drying of the solid;
d) optionally a calcination of the solid;
e) shaping of the solid into shaped bodies; and
f) optionally a calcination of the shaped bodies;
g) adjustment of the reduction level of the copper-comprising fraction of the adsorption composition to a value of at least 45% and at most 75%.

During this, after the complete reduction with hydrogen, the reduction level is adjusted to the desired value by oxidation of the adsorption composition precursor. During this, the residual hydrogen present is flushed from the reaction vessel with nitrogen, the desired oxidation temperature is set and a small proportion of oxygen is mixed into the nitrogen stream.

Depending on the selected adsorber size, the maximum uptake capacity of the adsorption composition for carbon monoxide comprised therein is sooner or later reached, so that it must be regenerated.

WO 2007/093526 also discloses the regeneration of the copper, zinc and zirconium oxide-comprising adsorption composition after the use thereof for the adsorptive removal of carbon monoxide from carbon monoxide-comprising substance streams by passing an inert gas such as for example nitrogen, methane or argon over the adsorption composition at a temperature of preferably at least 150° C. and at most 400° C. WO 2007/093526 also discloses the addition of oxygen in traces, in general in a proportion of at least 1 ppm, preferably at least 5 ppm and particularly preferably at least 10 ppm, in general at most 300 ppm, preferably at most 250 ppm and particularly preferably 200 ppm to the inert gas, preferably nitrogen or argon.

During the regeneration, the reduction level of the copper-comprising fraction of the adsorption composition can increase. However, at very high reduction levels, for example of 85%, a further rise in the reduction level can lead to an abrupt fall in the uptake capacity of the adsorption composition for CO. Particularly with multiple regeneration the danger exists that a certain critical reduction level will be exceeded and the uptake capacity of the adsorption composition falls.

An excessively low reduction level also has an adverse effect on the uptake capacity of the adsorption compositions for carbon monoxide. At a reduction level of <50%, the uptake capacity is already markedly lowered and is now only ca. 40% of the uptake capacity at a reduction level of 70%.

BRIEF SUMMARY

The objective of the invention is to provide an improved process for the regeneration of a copper, zinc and zirconium oxide-comprising adsorption composition after the use thereof for the adsorptive removal of carbon monoxide from substance streams comprising carbon monoxide and olefins. In particular the objective of the invention is to provide an improved process for the removal of carbon monoxide from substance streams comprising carbon monoxide and at least one olefin, wherein the uptake capacity of the adsorption material lies in an optimal range.

The problem is solved by a process for the activation of a copper, zinc and zirconium oxide-comprising adsorption composition for the adsorptive removal of carbon monoxide from substance streams comprising carbon monoxide and at least one olefin, wherein
(i) in a first activation step an activation gas mixture comprising the olefin and an inert gas is passed through the adsorption composition, and
(ii) in a second activation step the adsorption composition is heated to a temperature in the range from 180 to 300° C. and an inert gas is passed through it,
wherein the steps (i) and (ii) can each be performed several times.

DETAILED DESCRIPTION OF THE PREFERRED EMBODIMENTS

Figure 1:
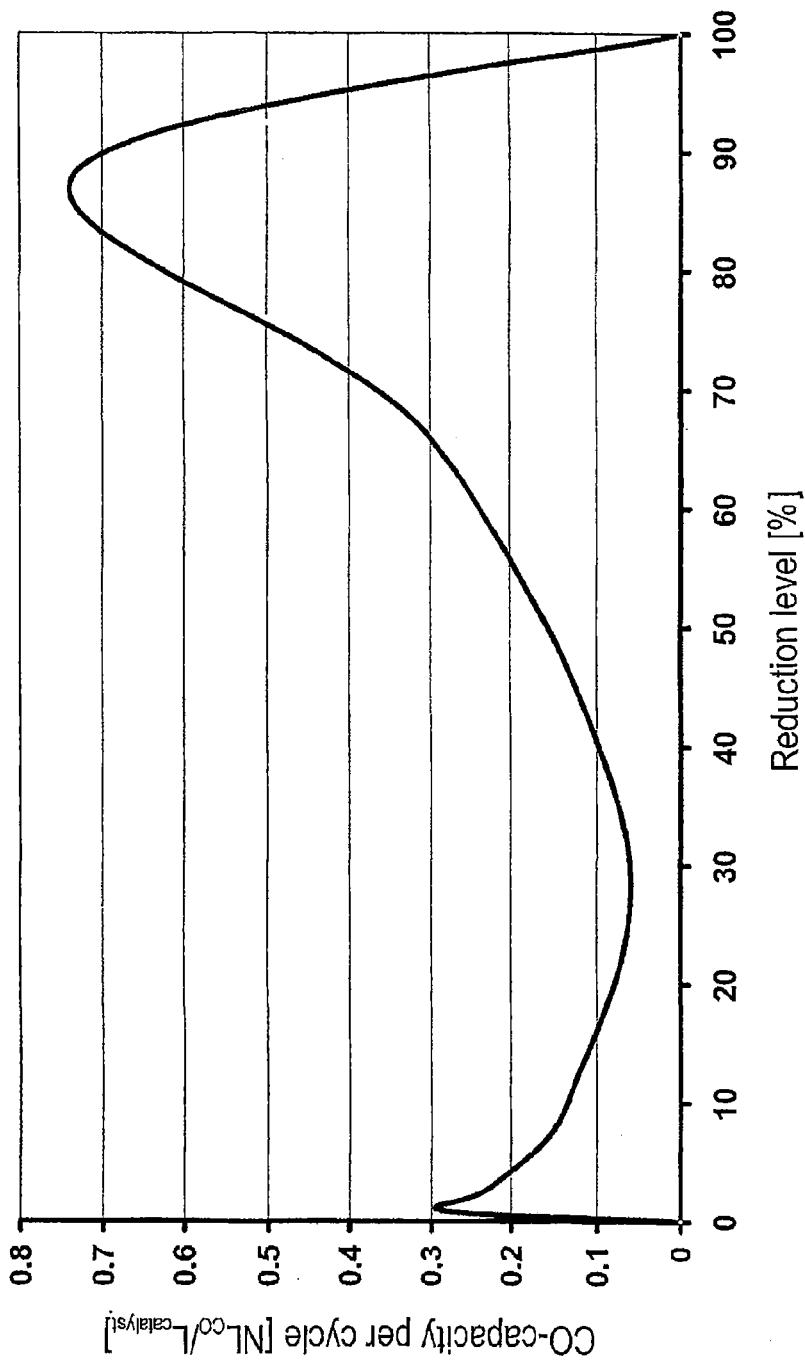
FIG. 1 is a chart showing the CO uptake capacity of the adsorption composition as a function of the reduction level R.

It was found that during the treatment of the adsorption composition in an inert gas stream at a temperature in the range from 180 to 300° C. the reduction level of the copper-comprising fraction of the adsorption composition increases if an olefin was previously adsorbed onto the adsorption composition. Olefins adsorbed onto the adsorption composition presumably act as reducing agents here and are themselves oxidized to carbon dioxide and water by oxygen bound in the adsorption composition. During this, copper(I) and/or copper(II) comprised in the adsorption composition is reduced to copper or copper(I).

XPS measurements have moreover shown that the freshly prepared catalyst is coated with a thin passivating layer of CuO and $Cu(OH)_2$. By treatment with pure inert gas without addition of oxygen, CuO and $Cu(OH)_2$ in the passivating layer are reduced to $Cu_2O$ by adsorbed olefin and the adsorption composition is thereby activated. As a result of this, the CO uptake capacity climbs considerably.

Thus, before the first adsorption step for the removal of CO from olefin, generally liquid, the adsorption composition is activated in that in a first treatment step (i) an activation gas stream which comprises the gaseous olefin, preferably gaseous propylene, is passed through it and then in a second step (ii) pure inert gas, in general nitrogen, is passed through it.

The activation gas stream used in step (i) in general comprises 1 to 100 vol. %, prefer-ably 5 to 75 vol. %, in particular 10 to 50 vol. % of the olefin. In the first treatment step (i), the GHSV is in general 100 to 5,000 $hrs^{-1}$, preferably 200 to 1,000 $hrs^{-1}$, the treatment time is in general 0.5 to 10 hrs, preferably 1 to 5 hrs, and the temperature of the adsorption composition is in general 0 to 100° C., preferably 15 to 50° C.

In the treatment step (ii) that follows, the adsorption composition is heated to a temperature in the range from 180 to 300° C., preferably 190 to 270° C., in particular 200 to 250° C. and the pure inert gas is passed through the adsorption composition. In this regeneration step, the GHSV is in general at least 100 $hrs^{-1}$, preferably at least 200 $hrs^{-1}$. It is in general at most 5,000 $hrs^{-1}$, preferably at most 1,000 $h^{-1}$. Here the treatment time is in general 0.5 to 24 hrs, preferably 1 to 10 hrs.

The pressure during the activation is in general 0.5 to 5 bar, preferably 1 to 3 bar.

The steps (i) and (ii) can also be performed several times. In general, they are each performed alternately 1 to 10 times, for example 2 to 4 times.

The activation comprising the steps (i) and (ii) is preferably performed when the copper-comprising fraction of the adsorption composition exhibits a reduction level of less than 65%. In particular, it is performed when the reduction level is less than 50%. Even an adsorption composition with a reduction level of the copper-comprising fraction of 0%, i.e. an adsorption composition which comprises copper exclusively in the form of Cu(II), can be regenerated in this manner.

Preferably the copper-comprising fraction of the adsorption composition exhibits a reduction level of at least 65% and at most 75% after the activation has been performed.

The reduction level is a measure of the oxide content of the copper comprised in the adsorption composition according to the invention. The reduction level is determined as the weighted substance content ratio of reduced copper, i.e. copper in the oxidation state 0 ($Cu^0$) or 1 ($Cu^1$) to the total copper, according to the formula:

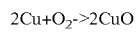

$$\text{Reduction level} = \frac{n(CuO) \cdot 0 + n(Cu_2O) \cdot 0.5 + n(Cu^0) \cdot 1}{n(CuO) + n(Cu_2O) + n(Cu^0)}$$

where n means the substance content in mole.

Pure metallic copper would have a reduction level of 100%, pure CuO a reduction level of 0%, and pure $Cu_2O$ a reduction level of 50%. However, a certain reduction level does not necessarily mean that the adsorption composition according to the invention comprises metallic copper or CuO. A certain reduction level can result through any possible composition of appropriate proportions of metallic copper, $Cu^0$, $Cu_2O$ or CuO.

The reduction level is determined by any procedure that is capable of quantitatively determining copper at its various oxidation levels. Particularly simple however is the complete oxidation of the copper in a sample of the adsorption composition by contacting with air at a temperature of at least 250° C. and at most 500° C. until constant weight, which is normally reached after at least 10 minutes and at most 12 hours. The reduction level of the sample is calculated from the weight gain of the sample under the assumption that additional weight is exclusively oxygen and assuming the following stoichiometry for the oxidation:

$2Cu + O_2 \rightarrow 2CuO$ or $2Cu_2O + O_2 \rightarrow 4CuO$

The following then applies:

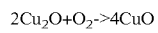

$$\text{Reduction level} = \frac{100}{\frac{M_{Cu} \cdot y_{CuO}}{M_{CuO} \cdot 100} - \frac{y_{CuO}}{100}} \cdot \left[ \frac{1}{\frac{\Delta m}{100} + 1} - 1 \right],$$

wherein
M is the molar mass of the relevant component Cu or CuO,
$y_{CuO}$ is the mass proportion of CuO based on the sum of the oxides of the completely oxidized catalyst, and
$\Delta m$ is the relative mass gain in % due to total oxidation.

The reduction level of the activated adsorption composition is in general at least 60%, preferably at least 65% and in general at most 80%, preferably at most 75%.

Also a subject of the invention is a process for the removal of carbon monoxide from substance streams comprising carbon monoxide and at least one olefin by adsorption on a copper, zinc and zirconium oxide-comprising adsorption composition comprising activation steps, adsorption steps and regeneration steps, wherein for the activation (i) in a first activation step an activation gas mixture comprising the olefin and an inert gas is passed through the adsorption composition, and (ii) in a second activation step the adsorption composition is heated to a temperature in the range from 180 to 300° C. and an inert gas is passed through it, wherein the steps (i) and (ii) can each be performed several times, in the adsorption steps the adsorption composition is contacted with the substance stream comprising carbon monoxide, and in the regeneration steps the adsorption composition is heated to a temperature in the range from 180 to 300° C. and a regeneration gas is passed through it, and the regeneration gas comprises 1000 to 3000 ppm of oxygen in an inert carrier gas.

It was found that during the regeneration of the adsorption composition in an inert gas stream the reduction level of the copper-comprising fraction of the adsorption composition increases. Presumably during the desorption process carbon monoxide is oxidized to carbon dioxide, whereby at the same time copper(I) and/or copper(II) comprised in the adsorption composition is correspondingly reduced. In addition, olefins adsorbed on the adsorption composition which derive from the substance stream to be purified from CO presumably likewise act as reducing agents, during which they themselves are presumably oxidized to carbon dioxide and water.

Through the presence of 1000 to 3000 ppm, preferably 1000 to 1900 ppm of oxygen in the regeneration gas, the reduction of copper in the adsorption composition is counteracted, in that a moderate reoxidation of copper reduced by CO and/or olefin takes place. It was found that with a concentration of 1000 to 3000 ppm of oxygen, the reduction level during the regeneration process changes only slightly or even remains essentially unchanged. Particularly good results are achieved with an oxygen content of 1300 to 1500 ppm. Naturally a particularly preferred inert gas is nitrogen, but other carrier gases chemically inert towards the adsorption composition are also possible, for example argon.

In the regeneration step, the GHSV is in general at least 100 $hrs^{-1}$, preferably at least 200 $hrs^{-1}$. It is in general at most 5,000 $hrs^{-1}$, preferably at most 1,000 $hrs^{-1}$. With an adsorption composition of the composition 70 wt. % CuO, 20 wt. % ZnO and 10 wt. % $ZrO_2$ and with a density of 1.35, the oxygen quantity used in the regeneration step is for example 2.3±0.5 normal liters per liter of catalyst. The oxygen quantity based on the catalyst mass is then for example 1.7±0.35 normal liters per kilogram of catalyst.

The duration of the regeneration is in general at least 1 hour, preferably at least 10 hours and particularly preferably at least 15 hours, and in general at most 100 hours, preferably at most 50 hours and particularly preferably at most 30 hours.

The adsorption composition activated and regenerated according to the invention is well suited for the purification of substance streams comprising one or more olefins. These are in general used in liquid form. Normal olefins which are freed from CO with the adsorption compositions used and regenerated according to the invention are ethene, propylene, 1-butene, 2-butene, 1,3-butadiene and/or styrene. The adsorption composition is particularly suitable for the removal of carbon monoxide (CO) from liquid propylene.

Before implementation of the adsorption steps and after implementation of the regeneration steps, the regeneration composition according to the invention preferably exhibits a reduction level of the copper-comprising fraction of 60 to 80%. The reduction level should not exceed 90%, preferably 85%.

In particular, the reduction level of the copper-comprising fraction is 65 to 75%. The adsorption composition admittedly does not then exhibit the maximal adsorption capacity of such compositions for CO, but it is considerably more regenerable than compositions with a higher reduction level and higher CO uptake capability. In particular, in this range the danger that a certain critical reduction level will be exceeded by the regeneration and that the uptake capacity for CO decreases markedly is very slight. It is thus also outstandingly suitable for freeing substance streams with greatly fluctuating CO content from CO in plants with two adsorbers, whereof at a given time one is being used for the adsorption and one is being regenerated.

The adsorption composition used according to the invention comprises copper, zinc and zirconium oxides. Copper can also partly be present as metallic copper and otherwise is present in the form of Cu(I) and Cu(II) oxides. In the pure form, the adsorption composition according to the invention in general comprises copper in a quantity which calculated as CuO corresponds to at least 30 wt. %, preferably at least 50 wt. %, and particularly preferably at least 60 wt. %, and in general at most 99.8 wt. %, preferably at most 90 wt. % and particularly preferably at most 80 wt. % of copper oxide CuO, each based on the total quantity of the adsorption composition. In the pure form, the adsorption composition according to the invention in general comprises zinc oxide ZnO in a quantity of at least 0.1 wt. %, preferably at least 5 wt. %, and particularly preferably at least 10 wt. %, and in general at most 69.9 wt. %, preferably at most 40 wt. % and particularly preferably at most 30 wt. %, each based on the total quantity of the adsorption composition. Further, in the pure form, it in general comprises zirconium oxide $ZrO_2$ in a quantity of at least 0.1 wt. %, preferably at least 3 wt. %, and particularly preferably at least 5 wt. %, and in general at most 69.9 wt. %, preferably at most 30 wt. % and particularly preferably at most 20 wt. %, each based on the total quantity of the adsorption composition. The zirconium dioxide fraction in the adsorption composition can be partially replaced by aluminum oxide $Al_2O_3$. For example at least 1%, at least 10% or at least 30% and at most 90%, at most 80% or at most 70% of the zirconium oxide fraction in the adsorption composition can be replaced by aluminum oxide. In the context of this invention, "pure form" means that apart from the copper (oxide), zinc oxide and zirconium oxide (this optionally partially replaced by aluminum oxide) fractions, no other components are comprised, apart from insignificant components which are for example entrained from the fabrication, such as residues of starting substances and reagents, additives for shaping and the like. "Pure form" thus means that the adsorption composition consists of the stated components.

The percentage contents of the adsorption composition always add up to 100 wt. %.

A very suitable adsorption composition consists in the pure form of 65-75 wt. % CuO, 15 to 25 wt. % ZnO and 5 to 15 wt. % $ZrO_2$, for example of ca. 70 wt. % CuO, ca. 20 wt. % ZnO and ca. 10 wt. % $ZrO_2$, and the proportions thereof add up to 100 wt. %.

The adsorption composition used according to the invention can be, but does not absolutely have to be, present in the pure form. It is possible to mix it with additives or to apply it onto an inert support. Suitable inert supports are the known catalyst supports such as for example aluminum oxide, silicon dioxide, zirconium dioxide, alumosilicates, clays, zeolites, diatomaceous earth and the like.

The adsorption composition used according to the invention is produced like known oxide catalysts. A convenient and preferred process for the production of the adsorption composition used according to the invention comprises the following process steps in the stated order:

a) preparation of a solution of the components of the absorption composition and/or of soluble starting compounds for these;
b) precipitation of a solid from this solution by addition of a base;
c) separation and drying of the solid;
d) optionally a calcination of the solid;
e) shaping of the solid into shaped bodies;
f) optionally a calcination of the shaped bodies;
with the proviso that at least one of the two calcination steps d) or f) is performed, and after or simultaneously with step f) there is performed step
g) adjustment of the reduction level of the copper-comprising fraction of the adsorption composition, expressed as the weight ratio of metallic copper to the sum of metallic copper and copper oxides, calculated as CuO, to a value of at least 60% and at most 80%.

In the first process step, step a), a solution of the components of the adsorption composition is prepared in the usual way, for example by dissolution in an acid such as nitric acid. Optionally, instead of the components of the adsorption composition, the starting materials for these, for example the nitrates, carbonates or hydroxy-carbonates of the metals are dissolved in an aqueous solution, which can also be acidic, for example comprise nitric acid. The quantity ratio of the salts in the solutions is calculated stoichiometrically and adjusted according to the desired final composition of the adsorption composition.

In step b) a solid is precipitated from this solution as the precursor of the adsorption composition. This is effected in the usual way, preferably by increasing the pH of the solution by addition of a base, for example by addition of sodium hydroxide solution or soda solution.

Before the drying in step c), the solid precipitation product formed is as a rule separated from the supernatant solution, for example by filtration or decantation, and washed free of soluble components, such as sodium nitrate, with water. Before the further processing, the precipitation product is then normally dried by normal drying methods. In general a treatment at slightly elevated temperature suffices for this, for example at least 80° C., preferably at least 100° C. and particularly preferably at least 120° C., over a period from 10 min to 12 hours, preferably 20 min to 6 hours and particularly preferably from 30 min to 2 hours. It is also possible and particularly convenient to convert the product of the precipitation by spray-drying to a dry powder which can be further processed, either directly—a certain alkali, for example sodium, content in the adsorption composition does not in general interfere—or after washing.

Following the drying, the precipitated and dried adsorption composition preproduct is optionally subjected to the calcination step d). The calcination temperature used for this is in general at least 250° C., preferably at least 300° C. and particularly prefer-ably at least 350° C., and in general at most 500° C., preferably at most 450° C. and particularly preferably at most 410° C. The calcination time is in general at least 10 minutes, preferably at least 20 minutes and particularly preferably at least 30 minutes and in general at most 12 hours, preferably at most 6 hours and particularly preferably at most 4 hours. The drying step c) and the calcination step d) can merge directly one into to the other.

After the drying step c) or the calcination step d), the adsorption composition or precursor thereof is processed in the shaping step e) with normal shaping processes such as extrusion, tabletting or pelleting into shaped bodies such as extrudates, tablets or—also spherical—pellets.

After the shaping step, the adsorption composition or precursor thereof is optionally subjected to a calcination step f). The calcination conditions to be used in step f) are identical with those of the calcination step d).

In the course of its production, the adsorption composition is subjected to at least one of the two calcination steps d) or f), and also optionally both. In the calcination step or steps, the adsorption composition precursor is converted into the actual adsorption composition and as usual the BET surface area and the pore volume of the adsorption composition inter alia are also established, during which, as is known, the BET surface area and the pore volume decrease with increasing calcination time and calcination temperature.

Preferably calcination is performed at least long enough overall for the carbonate content (calculated as $CO_3^{2-}$) of the adsorption composition to be at most 10 wt. %, based on the total weight of the calcination product, and its BET surface area to have a value in the range from at least 40 to at most 100 $m^2/g$. The pore volume of the adsorption composition, measured as water uptake, is adjusted to a value of at least 0.05 ml/g during the calcination. These values are preferred for the adsorption composition according to the invention.

The adsorption composition used according to the invention can also, as aforesaid, be deposited on a support. This is effected by normal impregnation processes or deposition precipitation processes. As is known, a deposition precipitation process is a precipitation process in the presence of a support or a support precursor. To effect a deposition precipitation process, in the precipitation process described above a support or support precursor is preferably added to the solution prepared in step a). If the support is already in the form of preshaped finished shaped bodies, i.e. a pure impregnation process, the shaping step e) is omitted, otherwise the support is also shaped in the course of the processing of the adsorption composition preproduct by precipitation, drying, calcination and shaping.

A preferred impregnation process for the production of the adsorption composition according to the invention is performed with preshaped supports and comprises the following process steps in the stated order:
a) production of a solution of the components of the absorption composition and/or of soluble starting compounds for these;
b) impregnation of a preshaped support with this solution;
c) drying of the impregnated support; and
d) calcination of the impregnated and dried support,
wherein after or simultaneously with step d) there is performed step
e) adjustment of the reduction level of the copper-comprising fraction of the adsorption composition, expressed as the weight ratio of metallic copper to the sum of metallic copper and copper oxides, calculated as CuO, to a value of at least 60% and at most 80%.

Process step a) of this impregnation process is performed like the step a) of the precipitation process described above. In step b), a preshaped support is impregnated with the solution. The preshaped support has a shape corresponding to the use purpose, for example extrudates, tablets or—also spherical— pellets. The impregnation is performed either with excess solution or with the quantity of solution corresponding to the pore volume of the support ("incipient wetness"). After the impregnation, the impregnated support is dried and calcined in steps c) and d) like the precipitation product in the precipitation process. However, with a preshaped support the shaping step is omitted.

Both in a precipitation and also in an impregnation process, a step for adjustment of the reduction level of the copper is necessary. This can be effected by establishment of suitable process conditions in the calcination (in particular calcination under an atmosphere not completely oxidizing copper) or in a separate process step after the calcination, where in the latter case the adjustment of the reduction level does not necessarily have to take place directly after the calcination. The adjustment of the reduction level is effected with any known process which is suitable for modifying the oxidation level of copper. If copper is mainly present in reduced form, it is reacted with oxygen, and with hydrogen if copper is mainly present in oxidized form.

Mostly, the calcination is performed under air, and consequently copper is present in the form of CuO in the precursor of the adsorption composition according to the invention obtained after the calcination. The reduction level is then adjusted by reduction of the copper to the desired reduction level. This is effected by treatment of the precursor present after the calcination with a reducing agent. Any reducing agent capable of reducing copper can be used. The exact reduction conditions to be used are dependent on the precursor and the composition thereof and on the reducing agent used and can easily be determined in a few routine experiments. A preferred process is treatment of the precursor with hydrogen, mostly by passing a hydrogen-comprising gas, preferably a hydrogen/nitrogen mixture, over it at elevated temperature.

It is also possible firstly to reduce the precursor of the adsorption composition used according to the invention completely and then to oxidize it to the desired reduction level. The complete reduction of the precursor of the adsorption composition is effected by reduction of the copper comprised in the adsorption composition to copper metal. This can in principle be effected with any reducing agent which can reduce the copper from the oxidation states I or II to oxidation state 0. This can be effected with liquid or dissolved reducing agents, and in this case drying is necessary after the reduction. Hence reduction with a gaseous reducing agent is very much more convenient, above all reduction with hydrogen by passing a hydrogen-comprising gas over it. The temperature to be used in this is in general at least 100° C., preferably at least 140° C. and particularly preferably at least 160° C. and in general at most 250° C., preferably at most 220° C. and particularly preferably at most 200° C. A suitable temperature is for example ca. 180° C. The reduction is exothermic. The quantity of reducing agent added should be adjusted so as not to depart from the selected temperature window. The progress of the activation can be followed on the basis of the temperature measured in the adsorption agent bed ("temperature-programmed reduction, TPR").

A preferred method for the reduction of the adsorption composition precursor is to establish the desired reduction temperature after a drying performed under a nitrogen stream and to add a small proportion of hydrogen to the nitrogen stream. For example a suitable gas mixture initially comprises at least 0.1 vol. % hydrogen in nitrogen, preferably at least 0.5 vol. % and particularly preferably at least 1 vol. %, and at most 10 vol. %, preferably at most 8 vol. % and particularly preferably at most 5 vol. %. A suitable value is for example 2 vol. %. This initial concentration is either maintained or increased, in order to reach and maintain the desired temperature window. The reduction is complete when in spite of constant or increasing levels of the reducing agent the temperature in the composition bed decreases or hardly any more water of reduction is formed. A typical reaction time is in general at least 1 hour, preferably at least 10 hours and in general at most 100 hours, preferably at most 50 hours.

The drying of the precursor of the adsorption composition, if necessary, is effected by heating the precursor to a temperature of in general at least 100° C., preferably at least 150° C. and particularly preferably at least 180° C. and in general at most 300° C., preferably at most 250° C. and particularly preferably at most 220° C. A suitable drying temperature is for example ca. 200° C. The precursor is kept at the drying temperature until only no longer interfering residues of adhering moisture are still present; this is in general the case after a drying time of at least 10 minutes, preferably at least 30 minutes and particularly preferably at least 1 hour and in general at most 100 hours, preferably at most 10 hours and particularly preferably at most 4 hours. The drying is preferably effected in a gas stream in order to transport the moisture out of the bed. Dry air can for example be used for this, however it is particularly preferable to pass an inert gas through the bed, and nitrogen or argon are particularly suitable here.

After the complete reduction, the reduction level is adjusted to the desired value by oxidation of the adsorption composition precursor. This can be effected with any known oxidizing agent capable of oxidizing copper. Oxygen is conveniently used for this, in particular air or an oxygen/nitrogen or air/nitrogen mixture ("lean air"). A preferred method for the oxidation of the adsorption composition precursor is to stop the hydrogen feed after the reduction, flush the residual hydrogen from the reaction vessel with nitrogen, and then adjust to the desired oxidation temperature and mix a small proportion of oxygen into the nitrogen stream. Temperature, total gas volume, oxygen content and treatment time must be optimized by routine experiments with determination of the reduction level for each individual case. A typical suitable gas mixture comprises for example at least 0.05 vol. % oxygen in nitrogen, preferably at least 0.1 vol. % and particularly preferably at least 0.15 vol. % and at most 0.5 vol. %, preferably at most 0.4 vol. % and particularly preferably at most 0.25 vol. %. A suitable value is for example 0.2 vol. %. A typical oxidation time is in general at least 24 hours, preferably at least 48 hours and particularly preferably at least 60 hours and in general at most 100 hours, preferably at most 90 hours and particularly preferably at most 80 hours. For example, oxidation is performed for 70 hours. The gas volume to be used is typically at least 50 NL gas per liter of adsorption composition precursor and hour (NL=normal liter, i.e. based on 0° C. and normal pressure), preferably at least 100 NL/l*hrs and particularly preferably at least 150 NL/l*hrs and in general at most 5,000 NL/l*hrs, preferably at most 1,000 NL/l*hrs, and particularly preferably at most 500 NL/l*hrs. For example, 200 NL/l*hrs is very suitable. The adjusted temperature is in general at least 30° C., preferably at least 35° C. and particularly preferably 40° C. and in general at most 80° C., preferably at most 70° C. and particularly preferably at most 60° C. For example 50° C. is very suitable.

For the use thereof, the adsorption composition shaped bodies are filled into a vessel described as an "adsorber", sometimes also "reactor", wherein they are contacted with the substance stream to be purified.

The finished adsorption composition is preferably dried (if necessary again) before its use for the adsorption of CO in order to remove traces of adhering moisture and to increase the adsorption capacity. The drying of the finished adsorption composition is performed like the drying of its precursor described above.

The adjustment of the reduction level and the drying are conveniently performed in the adsorber, since otherwise considerable effort is necessary to protect the ready-for-use activated adsorption composition from air and moisture during filling into the adsorber.

Following the adjustment of the reduction level and a possibly drying operation performed before or after the adjustment of the reduction level, the adsorption composition according to the invention is ready for use.

The adsorptive process according to the invention is particularly suitable for the removal of carbon monoxide from ethene, propene, 1-butene, 2-butene, 1,3-buta-diene, butene mixtures, butene/butadiene mixtures or styrene in order to lower the carbon monoxide content to values permissible for "polymer grade" olefins. In a quite especially preferred embodiment, carbon monoxide is adsorptively removed from liquid propene with the process according to the invention.

The adsorptive process according to the invention is particularly suitable for the removal of carbon monoxide from substance streams which in general comprise at least 0.001 ppm (for gases vol. ppm, for liquids wt. ppm), preferably at least 0.01 ppm and in general at most 1000 ppm, preferably at most 100 ppm and particularly preferably at most 10 ppm of carbon monoxide. For relatively high initial concentrations of carbon monoxide, it is usually more economical to perform a different known purification process such as distillation, catalytic oxidation of the carbon monoxide with oxygen to carbon dioxide or oxidation of the carbon monoxide with copper oxide with the formation of metallic copper and carbon dioxide beforehand, optionally with subsequent separation of carbon dioxide and oxygenation products, since otherwise the adsorption capacity of the adsorption composition can be reached too quickly.

For implementation of the adsorptive process according to the invention, the substance stream to be freed from carbon monoxide is passed over the bed of the adsorption composition shaped bodies according to the invention in the adsorber.

From the technical point of view, the temperature is not or not very critical for the adsorptive process according to the invention. Typical temperatures lie in the range from at least −270° C., preferably at least −100° C. and particularly preferably −40° C. and at most 300° C., preferably at most 200° C. and particularly preferably at most 100° C.

A significant parameter determining the depletion level is the contact time between substance stream and adsorption composition. This contact time is determined by the flow rate of the substance stream and the volume of the adsorption composition bed. Mostly, the volume flow of the substance stream to be purified is predetermined by the capacity of upstream or downstream units. Advantageously at least two adsorbers are provided, at least one of which can be exposed to a substance stream to be purified, while the adsorption composition is regenerated in at least one other.

Depending on the adsorber size selected, the maximum uptake capacity of the adsorption composition comprised therein for carbon monoxide is sooner or later reached, so that it must be regenerated.

For the regeneration of the adsorption composition according to the invention, firstly the substance stream to be purified is stopped, and it is preferably passed into a parallel adsorber filled with fresh or regenerated adsorption composition.

The invention is explained in more detail by the following examples.

EXAMPLES

The adsorption performance of an adsorption composition for the removal of CO from a propylene gas flow was systematically studied in a gas phase apparatus. The adsorption composition is the reduced form of an oxide precursor composition consisting of 70 wt. % CuO, 20 wt. % ZnO and 10 wt. % $ZrO_2$. For production of this oxide precursor composition, a Cu—Zn—Zr nitrate solution (metal content 15.2 wt. %, Cu:Zn:Zr ratio corresponding to a $CuO:ZnO:ZrO_2$ weight ratio of 7:2:1) was precipitated with soda solution (20 wt. %) at pH 6.5 and 70° C. After completion of precipitation, the suspension was stirred for a further 120 minutes at pH 6.5 and 70° C. Next, the solution was filtered, and the filter cake washed free of nitrate with demineralized water and dried at 120° C. The dried powder was calcined at 300° C. for 240 minutes in the forced air oven, then mixed with 3 wt. % graphite and compressed into 3×3 mm tablets with a side pressure of 50 N. The tablets were further calcined at 425° C. for 120 minutes.

The gas phase apparatus consisted of a reactor equipped with electrical jacket heating. The flow through the reactor was effected from top to bottom. The reactor had an internal diameter of 44.3 mm (DN40) and a length of 168 mm. The reusable thermoelement had an external diameter of 3.2 mm and 5 measurement points. The gas supply was provided by means of normal commercial mass flow controllers.

The carbon monoxide concentration was measured online via IR absorption.

The test conditions were as follows:
T: room temperature
p: 1 bar
Catalyst volume: 85 ml
Propylene flow: 150 NL×hrs$^{-1}$
GHSV: 1.765 hrs$^{-1}$
CO concentration: 100 ppm The integral CO uptake capacity of the adsorption composition was determined up to the breakthrough of CO, which was assumed to be when 10 vol. ppm of CO were measured in the reactor exit gas.

Determination of the CO Uptake Capacity as Function of Reduction Level

The CO uptake capacity of the adsorption composition as a function of the reduction level R was determined as follows:

For the determination of the CO uptake capacity as a function of the reduction level, several adsorption compositions with different reduction levels were specifically prepared and each one tested as described above.

The reduction level of the individual adsorption compositions was determined by the formula stated above.

A marked dependence of the CO uptake capacity on the reduction level of the copper was observed. The oxide material with R=0 displayed no CO uptake capacity. Up to an R of 2%, the uptake capacity rises rapidly to 0.3 NL CO (per liter of adsorption composition), then to fall again to 0.05 NL CO between R=2% and R=30%. Above R=30%, the CO uptake capacity then rises to an overall maximum of 0.8 NL CO. This maximum is reached at R=85 to 90%. Above R=90%, the CO uptake capacity falls abruptly, until at R=100% the material no longer displays any CO uptake capacity.

FIG. 1 presents the results of the measurements.

Because of the marked dependence of the CO uptake capacity on the reduction level, it is very important that the reduction level remains essentially constant during operation. A reduction level in the range from 65 to 75% is optimal, since the adsorption composition then already displays a sufficiently high uptake capacity of 0.4 NL CO, but there still exists a sufficient distance from the reduction levels which result in low uptake capacities.

Further Activation by Regeneration with Pure Inert Gas

As soon as the maximal CO uptake capacity of the adsorption composition was reached, a breakthrough of CO was observed. At this time point, the gas feed stream was stopped and the catalyst was heated to 200° C. for the regeneration. The minimum temperature for effective regeneration was 190° C. Below 180° C. no significant regeneration was observed. The regeneration was effected with industrial nitrogen at 200 to 250° C.

It was shown by IR that during the regeneration it was not CO, but $CO_2$, which is desorbed from the adsorption composition. In addition, adsorbed propylene is also oxidized by lattice oxygen atoms during the regeneration, whereby $CO_2$ is also formed. As a result, in every regeneration step which is performed with pure nitrogen the catalyst is reduced. The reduction level increases by 1.5 to 2% per regeneration step.

For example, a freshly prepared catalyst with an initial reduction level R of 77% displayed an increase in the CO adsorption capacity from adsorption step to adsorption step through regeneration with $N_2$. However, after about 7 regenerations, the CO uptake capacity began to fall markedly, since a critical reduction level was then exceeded.

Figure 2:
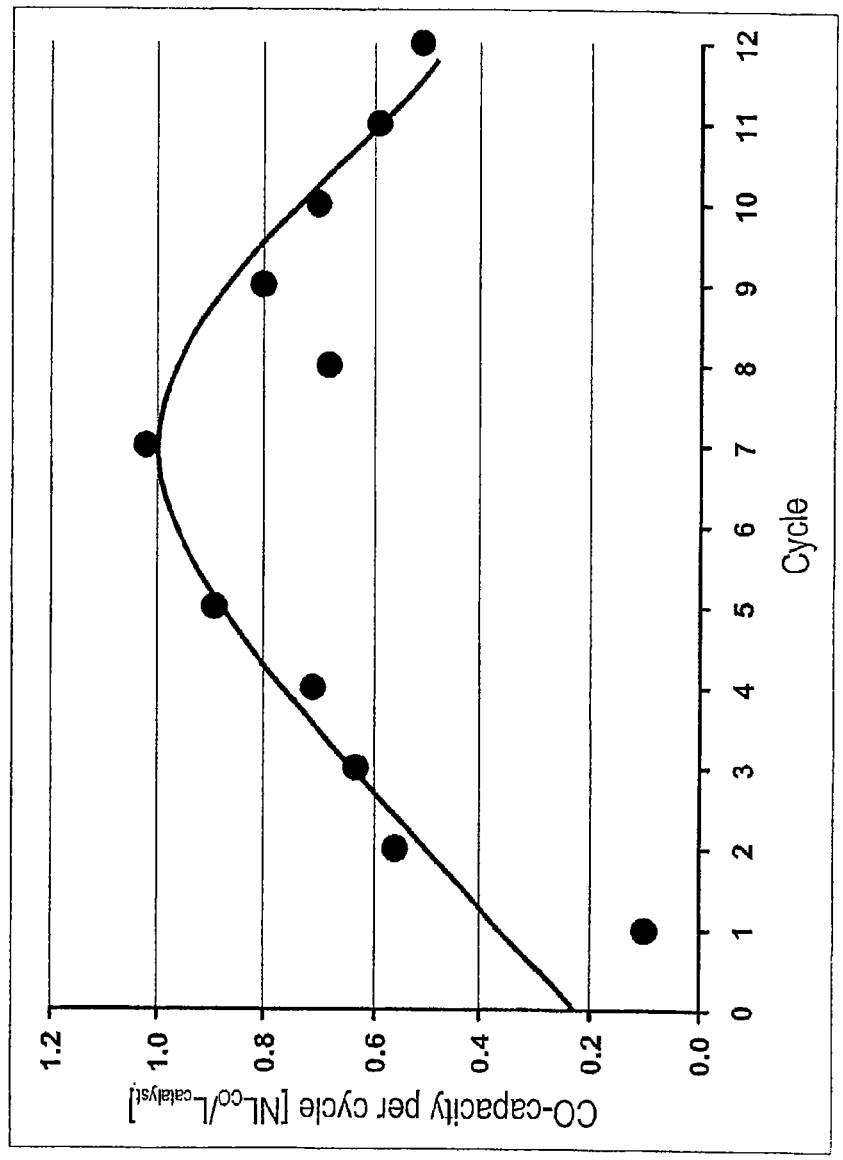
FIG. 2 presents the results of the experiments with an adsorption composition with an initial reduction level of 77%.

FIG. 2 presents the results of the experiments with an adsorption composition with an initial reduction level of 77%. Between two regeneration steps an adsorption step was performed each time, and the maximal CO uptake capacity determined.

In the first adsorption step, the freshly prepared adsorption composition in general displayed only a low CO uptake capacity. XPS measurements have shown that after the production of the catalyst, adsorption-active Cu(I) on the surface is coated with a thin layer of CuO and $Cu(OH)_2$. This layer impedes the adsorption of CO.

In the first regeneration cycle with the use of pure $N_2$ as the regeneration gas, the CuO and $Cu(OH)_2$-comprising layer was reduced to a layer of $Cu_2O$ by oxidation of the adsorbed species (CO and propylene). As a result of this, the CO uptake capacity in the second adsorption cycle increased markedly compared to the first adsorption cycle.

An adsorption composition with a lower initial reduction level R of only 67% needed more regeneration cycles, compared with an adsorption composition with an initial reduction level of 77%, until the optimal CO uptake capacity was reached.

Figure 3:
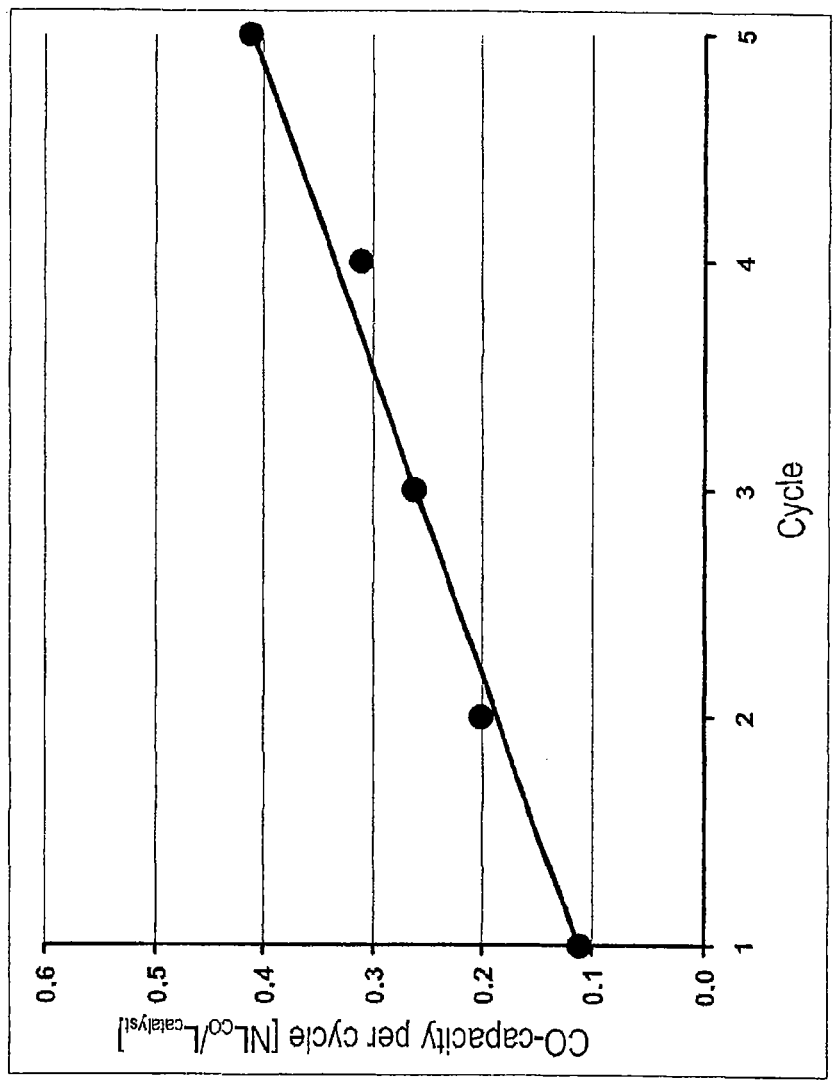
FIG. 3 presents the results of the regeneration of an adsorption composition with an initial reduction level of 67% with industrial nitrogen at 250° C.

FIG. 3 presents the results of the regeneration of an adsorption composition with an initial reduction level of 67% with industrial nitrogen at 250° C. Between two regeneration steps an adsorption step was performed each time, and the maximal CO uptake capacity determined.

Activation by Treatment with Propylene-Comprising Inert Gas and Pure Inert Gas (According to the Invention)

An untreated catalyst with a reduction level of 75% displayed a CO uptake capacity of only 0.08 NL CO per liter of adsorption composition in the first cycle. If the same catalyst was first treated for 1 hrs at 30° C. with a mixture of 50% propene and 50% $N_2$ at a GHSV of 1,765 hrs$^{-1}$, and then baked with industrially pure nitrogen at 250° C. for 3 hours, the CO uptake capacity increased to 0.55 NL CO per liter of adsorption composition.

Regeneration with Oxygen-Comprising Inert Gas

After the activation phase in which the regeneration was performed with industrially pure nitrogen, after each adsorption step the regeneration was performed with a nitrogen stream which comprises 1500 ppm oxygen. The temperature during this was 200° C. and the GHSV was 500 hrs$^{-1}$. Over a total period of 3 hours, 2.3 NL of oxygen were fed in per liter of catalyst.

Figure 4:
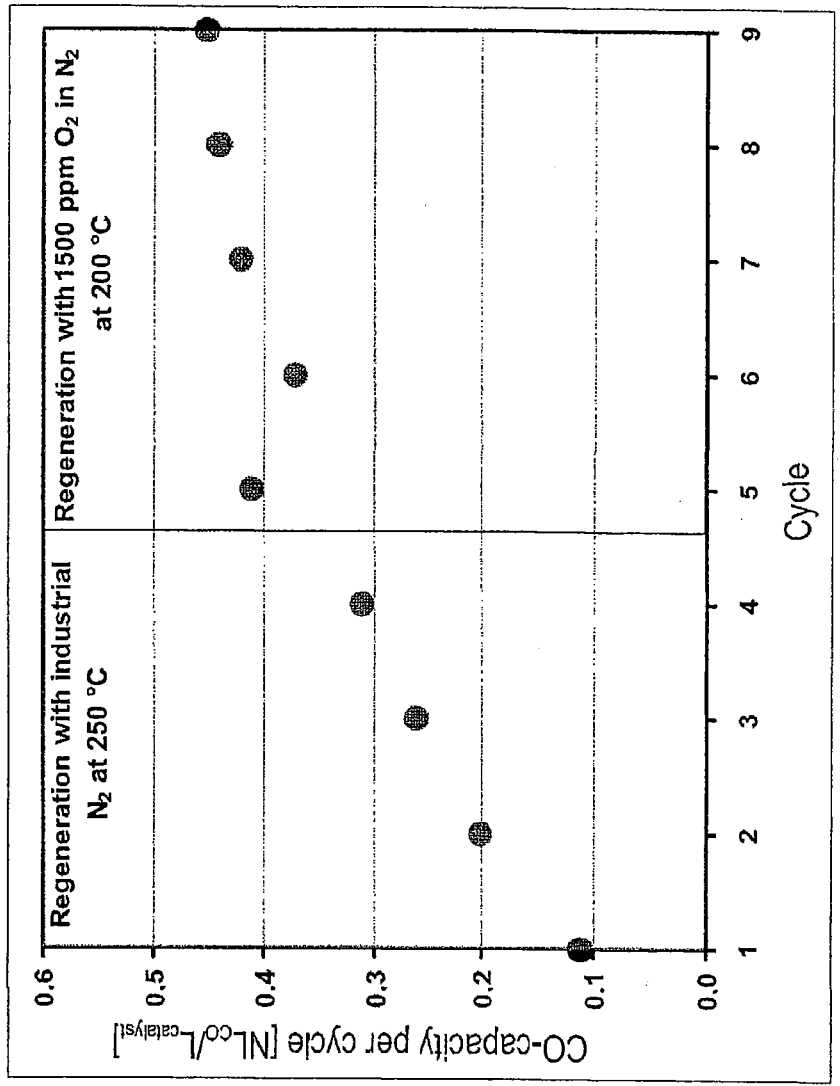
FIG. 4 shows the results of experiments in which regeneration steps 1 to 4 were performed with pure $N_2$ at 250° C. and the regeneration steps 5 to 9 at 200° C. with nitrogen comprising 1500 ppm $O_2$.

FIG. 4 shows the results of experiments in which regeneration steps 1 to 4 were performed with pure $N_2$ at 250° C. and the regeneration steps 5 to 9 at 200° C. with nitrogen comprising 1500 ppm $O_2$. Between each of these, an adsorption step was performed and the maximum CO uptake capacity determined.

As can be seen from FIG. 4, the result of regeneration with the oxygen-comprising regeneration gas was that the CO uptake capacity of the adsorption composition remained essentially constant.

The invention claimed is:

1. A process for the removal of carbon monoxide from substance streams comprising carbon monoxide and at least one olefin by adsorption on a copper, zinc and zirconium oxide-comprising adsorption composition comprising activation steps, adsorption steps and regeneration steps, wherein for the activation
- (i) in a first activation step an activation gas mixture comprising the olefin and an inert gas is passed through the adsorption composition, and
- (ii) in a second activation step the adsorption composition is heated to a temperature in the range from 180 to 300° C. and an inert gas is passed through it, wherein the steps (i) and (ii) can each be performed several times, in the adsorption steps the adsorption composition is contacted with the carbon monoxide-comprising substance stream, and in the regeneration steps the adsorption composition is heated to a temperature in the range from 180 to 300° C. and a regeneration gas is passed through it, wherein the regeneration gas comprises 1000 to 3000 ppm of oxygen in an inert carrier gas and the copper-comprising fraction of the adsorption composition after a regeneration step has a reduction level of at least 65% and at most 75%.

2. The process according to claim 1, wherein the adsorption composition comprises copper in a quantity which corresponds to 30 to 99.8 wt. % CuO, zinc in a quantity which corresponds to 0.1 to 69.9 wt. % ZnO and zirconium in a quantity which corresponds to 0.1 to 69.9 wt. % $ZrO_2$, each based on the total quantity of the adsorption composition.

3. The process according to claim 1, wherein the regeneration gas comprises 1300 to 1500 ppm oxygen.

4. The process according to claim 1, wherein carbon monoxide is removed from a liquid propylene stream.

* * * * *